United States Patent [19]

Morgan

[11] Patent Number: 4,867,821
[45] Date of Patent: Sep. 19, 1989

[54] PROCESS FOR FABRICATING SELF-ADHESIVE BANDAGES

[76] Inventor: Burton D. Morgan, 1790 Stoney Hill Dr., Hudson, Ohio 44236

[21] Appl. No.: 217,423

[22] Filed: Jul. 11, 1988

[51] Int. Cl.[4] .................. B32B 31/08; B32B 31/18
[52] U.S. Cl. .................... 156/152; 128/156; 156/267; 156/268; 156/269; 156/324
[58] Field of Search .............. 128/156; 156/152, 268, 156/269, 324, 267

[56] References Cited

U.S. PATENT DOCUMENTS 4,622,089  11/1986  Lauritzen .................. 156/324 X
4,753,232  6/1988   Ward ........................ 128/156
4,780,168  10/1988  Beisang et al. ............ 128/156 X Primary Examiner—Robert A. Dawson
Attorney, Agent, or Firm—Oldham & Oldham Co.

[57] ABSTRACT

A continuous process for fabricating strips of gel-coated, self-adhesive bandages in which a laminate comprising a release paper strip fastened to a bandage strip whose lateral wound-side surfaces are coated with a pressure-sensitive adhesive is withdrawn from a feedstock roll and passed over a delamination roll where the two strips are separated. The release paper strip is then passed over an embossing roll where it is longitudinally scored, while a gel composition is simultaneously deposited on the middle portion of the bandage strip. The two strips are thereafter forwarded to a relamination roll at which point they are united in a relamination, and sent to a die-cutting roll where the desired bandage shape is cut into the bandage strip. The die-cut relaminate is thereafter forwarded to a delamination roll where the selvedge is removed, leaving a strip of the desired bandages.

8 Claims, 2 Drawing Sheets

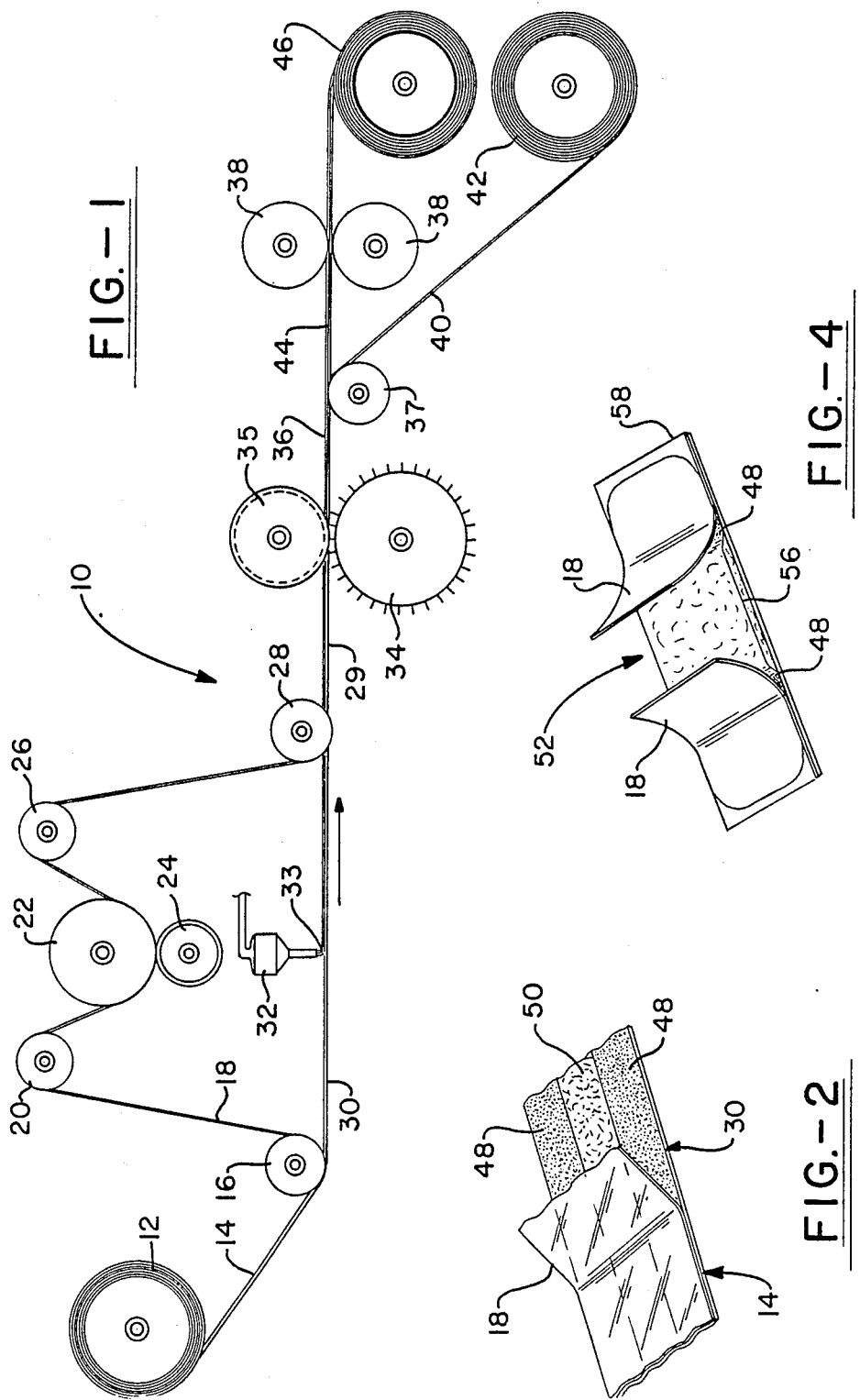

४,८६७,८२१

PROCESS FOR FABRICATING SELF-ADHESIVE BANDAGES

TECHNICAL FIELD

This invention relates to a process for the manufacture of bandages. More particularly, this invention relates to a process for manufacturing self-adhesive bandages having a hydrophilic coating in the center portion of the bandage adapted for deployment over a wound. Specifically, this invention relates to a method of continuously separating a backing paper strip from a strip of bandage fabric whose lateral portions are coated with a pressure-sensitive adhesive, covering the center portion of the bandage fabric with a hydrophilic gel coating while simultaneously longitudinally scoring the backing paper strip, thereafter relaminating the scored backing paper strip with the coated bandage fabric strip, and subsequently die-cutting the coating bandage fabric strip in desired bandage shapes.

BACKGROUND OF THE INVENTION

In applicant's co-pending application Ser. No. 07/217,422 and Filing Date of July 11, 1988 there is disclosed a self-adhesive bandage comprising a fabric carrier strip in which the surface facing the wound, i.e., the wound-side surface, is coated with a hydrophilic, gel-type coating, while the side portions of the surface are covered with a pressure-sensitive adhesive. The adhesive fastens a backing, or "release" paper to the wound-side surface of the bandage, maintaining its sterile character until removed. The middle of the release paper is transversely scored for easy removal prior to fastening the bandage to a wound. The hydrophilic nature of the gel-coated portion positioned adjacent to the wound prevents formation of an adhering bond between the wound and the bandage, allowing the latter's eventual removal without pain. The gel is also air-permeable, thus facilitating healing of the wound which it protects.

While the bandage described represents a significant advance over bandages previously known, in order to be successful, it must be capable of automated, low-cost manufacture. Furthermore, it is necessary that provision be made for placing the gel coating on the center portion of the bandage, between the adhesive coated portions of the bandage fabric. It is also necessary that the manufacturing process provide a way in which bandages of a desired shape can be formed so as to include a release paper covering that maintains the sterile quality of the bandage surface to be exposed to the wound, but which can be easily removed prior to use.

DISCLOSURE OF THE INVENTION

In light of the forgoing, therefore, it is the first aspect of this invention to provide a process for manufacturing self-adhesive bandages which exhibit no tendency to adhere or "stick" to wound which they are designed to protect.

It is the second aspect of this invention to provide a method for manufacturing a non-stick adhesive bandage which contains a hydrophilic gel coating between the bandage and its release paper covering.

A further aspect of this invention is to furnish a continuous, sterile method of fabricating non-stick self-adhesive bandages.

An additional aspect of this invention is the provision of a fabrication process which is capable of producing a self-adhesive bandage with an easily removable, scored release paper positioned over a bandage, the lateral portions of whose wound-side surface are coated with a pressure-sensitive adhesive, while the center portion of such surface is covered with a hydrophilic gel.

Another aspect of this invention is to provide a process for inexpensively fabricating self-adhesive bandages which can be applied to minor wounds by medically untrained individuals.

The preceding and other aspects of the invention are achieved, as will be made clear in the following detailed description of the invention, by a process for fabricating a strip of self-adhesive bandages comprising continuously separating a lamination of a release strip component attached to the wound-side surface of a bandage strip component, the lateral portions of said surface being covered with a pressure- sensitive adhesive, thereafter scoring said release strip component while simultaneously depositing a gel coating on the middle portion of said wound-side surface, thereafter relaminating said components in their original relationship, and thereafter die-cutting said fabric bandage strip component of the relamination in a desired bandage shape and separating the selvedge therefrom to form a strip of self-adhesive bandages.

The foregoing and still other aspects of the invention are provided by a process for manufacturing self-adhesive bandages wherein a bandage feedstock lamination comprising a release strip component adhesively fastened by means of a pressure-sensitive adhesive to the wound-side surface of a bandage strip component is withdrawn from a bandage feedstock roll by laminate transport means and delaminated by first delamination means in which said components are separated, said release strip component being thereafter passed between a score-embossing roll in contact with an anvil roll, and said bandage strip component having a gel-deposited on the middle portion of said surface by gel coating means, following which, said components are relaminated in their original relationship by relamination means, the relaminate being thereafter passed between a die roll in contact with an anvil roll where said bandage strip component of said relaminate is die-cut in a desired bandage shape, and thereafter the selvedge from the die-cut relaminate bandage strip is separated from the rest of said die-cut relaminate bandage strip by passing the die-cut relaminate over second delaminating means, thereby forming a strip of the desired bandages.

BRIEF DESCRIPTION OF THE DRAWINGS

The invention will be better understood in connection with following drawings, in which like numbers refer to like parts, and in which FIG. 1 is a schematic representation of the process of the invention.

FIG. 2 is an isometric view of a partially delaminated section of the feed stock laminate employed by the process of the invention.

FIG. 4 is a self-adhesive bandage of the kind produced by the process of the invention, with the release paper partially removed.

DETAILED DESCRIPTION OF THE INVENTION

Figure 3:
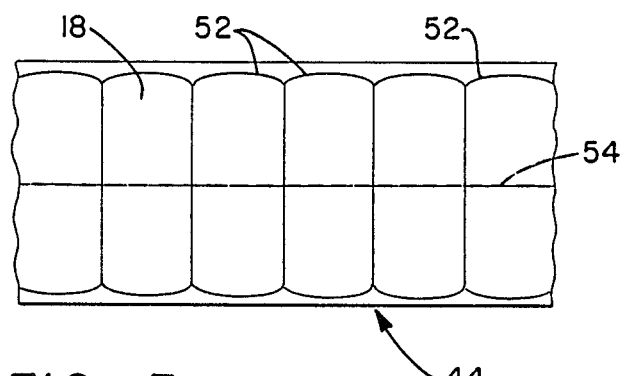
FIG. 3 is a plan view of a self-adhesive bandage strip produced by the process of the invention.

FIG. 1 is a schematic representation of the process of the invention showing a fabrication process train, generally 10, comprising a laminate feedstock roll 12 from which a laminate strip 14 is continuously being drawn. The laminate strip 14, more clearly shown in FIG. 2, comprises a release paper strip component 18, and a bandage strip component 30, the two components being held together by pressure-sensitive adhesive coated on the lateral portions of the wound-side surface of the bandage strip component. The laminate strip 14 is delaminated at delaminating roll 16, the release paper strip component proceeding onward to idler roll 20, while the bandage strip component is forwarded to gel applicator 32. From idler roll 20, the release paper strip component 18 moves forward to the bite between embossing roll 24 and anvil roll 22, both of which are usually driven, where the release paper strip component is scored, typically in the middle thereof, before advancing to idler roll 26. The middle portion of the wound-side surface of bandage strip component 30 is covered with a gel 33 dispensed from gel applicator 32, before passing on to relamination roll 28 where it is relaminated with the release paper strip component 18 in the components' original relationship. The relaminated strip 29 then proceeds to the bite between die roll 34 and anvil roll 35, both of which may be driven, where the bandage strip component is cut to the desired bandage shape. The die-cut relamination 36 is then forwarded to delamination roll 37, at which point the selvedge 40 is separated and sent to a driven selvedge wind-up roll 42, where it is gathered for subsequent disposal. The bandage strip 44 is pulled through the bite of draw-rolls 38, which furnish the primary motive force for the process, ultimately being wound on the driven bandage strip wind-up roll 46. The movement of the laminate stock through the process, as shown in the Figure, and as described, is from left to right, as indicated by the associated arrow. The speed of the process may be varied as desired, and will generally depend upon mechanical limitations, as is well known in the art. Commonly, however, the laminate stock 14 will be processed into the bandage strip 44 at a rate of from about 800 to 1200 inches per minute.

The gel applicator device 32 may take a variety of forms, it simply being necessary to deposit the gel on the middle portion of the bandage strip component. It has been found convenient to use a hollow needle for the purpose, either gravity or a positive pressure being used to force the gel through the device.

While FIG. 1 illustrates a movement of the laminate strip by the force exerted through the frictional grip of the draw-rolls 38 as the bandage strip 44 passes therebetween, other means well known to the art might also be used, for example, a sprocket gear which engages holes corresponding to its teeth, that may be positioned along the longitudinal axis of the laminate.

While a particular positioning and relative size of the various rolls described is illustrated in the Figure, positioning of the rolls may be varied within relatively broad limits, as can their diameters. The rotational speed of the rolls will depend upon factors including roll diameter, the desired processing rate, and similar factors.

FIG. 2 is an isometric view of a partially delaminated section of the laminate strip 14. As shown, the laminate is comprised of a release paper strip component 18, and a bandage strip component 30. The wound-side surface of the bandage strip component 30 is shown comprising lateral portions 48, which are coated with a pressure-sensitive adhesive, and a center portion 50 on which the gel formulation is deposited. The relative widths of the lateral portions 48, and the center portion 50 may be varied as desired; however, generally, each of the two pressure- sensitive adhesive coated portions 48 will constitute about a third of the width of the bandage strip component 30, with the center portion constituting the remaining one-third of the width. The bandage strip component commonly will be from about ¾ inch to 1¼ inches wide, although this may also be varied within broad limits. An overall width of about one inch has been found convenient to use in the case of bandages for most minor wounds. The thickness of the coatings may also vary; however, it has been found preferable to use an adhesive coating of about 1½ mils, in conjunction with a gel coating of about 2 mils in thickness.

Gels having different compositions may be used, although as indicated in the co-pending application referred to above, bandages of the type particularly contemplated by the invention are those involving gels containing from about 10% to 30%, by weight, of a polyacrylamide cross-linked with from about 0.02% to 0.6%, by weight, of a bis-functional cross-linking agent, for example, a bis-acrylamide. The cross-linked polymer is normally mixed with from 5% to 50% of a polyol such as sucrose or glycerol, with the remainder of the gel being water. Ordinarily gels containing from about 20% to 30%, by weight, of total solids are particularly useful in connection with the bandage strips contemplated by the invention.

The pressure-sensitive adhesives employed may be any of those commonly used in the art such as, for instance, acrylic adhesives, those made from elastomers, natural or synthetic, mixed with various resins, and similar compositions.

FIG. 3 is a plan view of a self-adhesive bandage strip, generally 44, produced by the process of the invention. As shown, the bandage strip component of the bandage strip 44, has been die-cut into a particular bandage shape 52, while the release paper strip component 18 has been scored along a line 54 located on the transverse middle of the release paper strip component 18. When the bandage strips 44 are cut into individual bandages of the type shown in FIG. 4, the scoring 54 facilitates removal of the covering release paper, as shown in FIG. 4. If desired, however, the bandage strips 44 can be dispensed from a box in which rolls of such strips are contained. When dispensed from rolls, the bandages 52 are simply peeled from the release paper strip component 18 and applied to a wound.

Figure 3A:
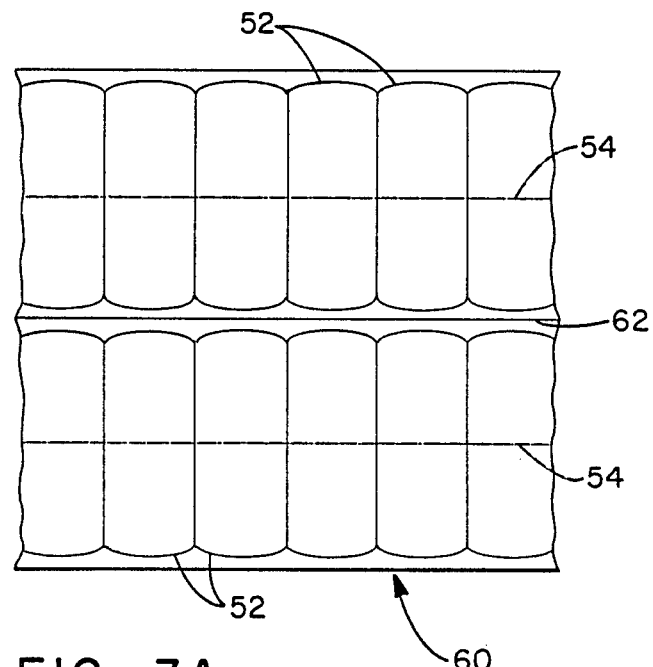
FIG. 3A is a plan view of a self-adhesive bandage strip of the kind contemplated by the invention containing two longitudinaly parallel strips of bandages.

FIG. 3A is a plan view of a multiple bandage strip, generally 60, containing two longitudinally parallel strips of bandages 52. If preferred, the two strips may be divided along line 62 which may be scored at the same time lines 54 are scored by embossing roll 24. While two strips of bandages are illustrated in the Figure, additional strips may also be incorporated in a multiple bandage strip and processed as described in connection with FIG. 1.

FIG. 4 is a self-adhesive bandage of the type produced by the process of the invention, generally 52, with the scored release paper 18 partially removed therefrom. The figure shows further detail of the gel coat deposited on the middle portion of the bandage, between the adhesive coated lateral portions 48. Various shapes of bandages may be produced according to the process of the invention, including square, rectangular, round, or other shapes.

The pressure-sensitive adhesive coating 48, and the gel-coat 56 are carried by a substrate 58. The substrate may be made from a variety of materials, however the use of a non-woven fabric, for example, cotton is preferred. While the thickness of the substrate may vary, a thickness of from about 2 to 5 mils provides a particularly sturdy bandage, and such thickness is preferred. Likewise, the release paper 18 may be made from a variety of materials other than paper; however, paper is preferred, preferably of a weight of from about 20 pounds to 100 pounds per ream. White sulfite paper or white coated kraft paper are particularly useful in the application.

Although the release paper strip component need not be scored, scoring greatly facilitates removal of the release paper and its presence is, therefore, especially useful. The dimensions of the bandage will naturally depend upon the use to which it is to be put; however, for minor wounds, rectangular of bandages of from about 2¼ inches to 3½ inches long by about ¾ inch to 1 inch wide will be used. A particularly useful bandage is one about 3 inches long by ⅜ inch wide.

While in accordance with the patent statutes, a preferred embodiment and best mode has been presented, the scope of the invention is not limited thereto, but rather is measured by the scope of the attached claims.

What is claimed is:

1. A process for fabricating a strip of self-adhesive bandages comprising continuously separating a lamination of a release strip component attached to the wound-side surface of a bandage strip component, the lateral portions of said surface being covered with a pressure-sensitive adhesive, thereafter scoring said release strip component while simultaneously depositing a gel coating on the middle portion of said wound-side surface, thereafter relaminating said components in their original relationship, and thereafter die-cutting said fabric bandage strip component of the relamination in a desired bandage shape and separating the selvage therefrom to form a strip of self-adhesive bandages.

2. A process according to claim 1 wherein said laminate is sufficiently wide to allow a plurality of longitudinally parallel strips of self-adhesive bandages to be simultaneously fabricated from said laminate.

3. A process according to claim 1 wherein said scoring is performed by passing said backing strip component between an embossing roll and an anvil roll, and said die-cutting is performed by passing said relamination between a die-roll and an anvil-roll.

4. A process for manufacturing self-adhesive bandages wherein a bandage feedstock lamination comprising a release strip component adhesively fastened by means of a pressure-sensitive adhesive to the wound-side surface of a bandage strip component is withdrawn from a bandage feedstock roll by laminate transport means and delaminated by first delamination means in which said components are separated, said release strip component being thereafter passed between a score-embossing roll in contact with an anvil roll, and said bandage strip component having a gel deposited on the middle portion of said surface by gel-coating means, following which, said components are relaminated in their original relationship by relamination means, the relaminate being thereafter passed between a die-roll in contact with an anvil roll where said bandage strip component of said relaminate is die-cut in the shape of a desired bandage, and thereafter the selvedge from the die-cut relaminate bandage strip is separated from the rest of said die-cut relaminate bandage strip by passing the die-cut relaminate over a second delaminating means, thereby forming a strip of the desired bandages.

5. A process according to claim 4 wherein said first and second delaminating means, respectively comprise delaminating rolls.

6. A process according to claim 4 wherein said gel coating means comprises a device positioned above said middle portion of said surface which is provided with an opening through which said gel passes immediately prior to being deposited on said surface.

7. A process according to claim 6 wherein said device is a hollow needle.

8. A process according to claim 4 wherein said laminate transport means comprises driven pull-rolls in contact with said relaminate.

* * * * *